United States Patent [19]
Wei

[11] Patent Number: 6,051,222
[45] Date of Patent: Apr. 18, 2000

[54] HUMAN MUTY

[75] Inventor: Ying-Fei Wei, Darnestown, Md.

[73] Assignee: Human Genome Sciences, Inc., Rockville, Md.

[21] Appl. No.: 09/277,960

[22] Filed: Mar. 29, 1999

Related U.S. Application Data

[62] Division of application No. 08/813,574, Mar. 7, 1997
[60] Provisional application No. 60/013,132, Mar. 11, 1996.

[51] Int. Cl.[7] .............................. A61K 38/46; C12N 9/24; C12P 21/06
[52] U.S. Cl. ......................... 424/94.6; 435/200; 435/69.1
[58] Field of Search ..................................... 530/350, 324, 530/402; 435/69.1, 186, 200; 514/12; 424/94.6

[56] References Cited

PUBLICATIONS

Au, K. G. et al., "*Escherichia coli* mutY gene product is required for specific A–G→C–G mismatch correction," *Proc. Natl. Acad. Sci. USA 85:*9163–9166 (1988).

Au, K. G. et al., "*Escherichia coli* mutY gene encodes an adenine glycosylase active on G–A mispairs," *Proc. Natl. Acad. Sci. USA 86:*8877–8881 (1989).

Bessho, T. et al., "Evidence for Two DNA Repair Enzymes for 8–Hydroxyguanine (7,8–Dihydro–8–oxoguanine) in Human Cells," *J. Biol. Chem. 268:*19416–19421 (1993).

Cabrera, M. et al., "mutM, a Second Mutator Locus in *Escherichia coli* That Generates G–C→T–A Transversions," *J. Bacteriol. 170:*5405–5407 (1988).

Claverys, J. –P. and Lacks, S. A., "Heteroduplex Deoxyribonucleic Acid Base Mismatch Repair in Bacteria," *Microbiol. Rev. 50:*133–165 (1986).

Jones, M. et al., "Repair of a Mismatch Is Influenced by the Base Composition of the Surrounding Nucleotide Sequence," *Genetics 115:*605–610 (1987).

Lieb, M., "Specific Mismatch Correction in Bateriophage Lambda Crosses by Very Short Patch Repair," *Mol. Gen. Genet. 191:*118–125 (1983).

(List continued on next page.)

*Primary Examiner*—Karen Cochrane Carlson
*Assistant Examiner*—Devesh Srivastava
*Attorney, Agent, or Firm*—Sterne, Kessler, Goldstein & Fox P.L.L.C.

[57] ABSTRACT

A human mutY polypeptide and DNA (RNA) encoding such polypeptide and a procedure for producing such polypeptide by recombinant techniques is disclosed. Also disclosed are methods for utilizing such polypeptide for preventing and/or treating diseases associated with a mutation in this gene. Diagnostic assays for identifying mutation in nucleic acid sequence encoding a polypeptide of the present invention and for detecting altered levels of the polypeptide of the present invention for detecting diseases, for example, cancer, are also disclosed.

14 Claims, 4 Drawing Sheets

OTHER PUBLICATIONS

Lieb, M., et al., "Very Short Patch Mismatch Repair in Phage Lambda: Repair Sites and Length of Repair Tracts," *Genetics 114*:1041–1060 (1986).

Lu, A.–L. and Chang, D.–Y., "Repair of Single Base–Pair Transversion Mismatches of *Escherichia coli* In Vitro: Correction of Certain A/G Mismatches is Independent of dam Methylation and Host mutHLS Gene Functions," *Genetics 118*:593–600 (1988).

Maki, H. and Sekiguchi, M., "MutT protein specifically hydrolyses a potent mutagenic substrate for DNA synthesis," *Nature 355*:273–275 (1992).

McGoldrick, J. P. et al., "Characterization of a Mammalian Homolog of the *Eschericia coli* MutY Mismatch Repair Protein," *Mol. Cell. Biol. 15*:989–996 (1995).

Michaels, M. L. et al., "MutY, an adenine glycosylase active on G–A mispairs, has homology to endonuclease III," *Nucl. Acids Res. 18*:3841–3845 (1990).

Michaels, M. L. et al., "Evidence that MutY, and MutM combine to prevent mutations by an oxidatively damaged form of guanine in DNA," *Proc. Natl. Acad. Sci. USA 89*:7022–7025 (1992).

Michaels, M. L. and Miller, J. H., "The Go System Protects Organisms from the Mutagenic Effect of the Spontaneous Lesion 8–Hydroxyguanine (7,8–Dihydro–8–Oxoguanine)," *J. Bacteriol.* (20):6321–6325 (1992).

Michaels, M. L. et al., "A Repair System for 8–Oxo–7, 8–dihydrodeoxyguanine," *Biochemistry 31*:10964–10968 (1992).

Modrich, P., "Mechanisms and Biological Effects of Mismatch Repair," *Annu. Rev. Genet. 25*:229–253 (1991).

Radany, E. H. "Expression Cloning of a Candidate Human MutY Homolog." *J. Cell. Biochem. Supp. 21A*:298, Abstract No. C5–240 (Mar./Apr. 1995).

Radicella, J. P. et al., "Some mismatch repair activities in *Escherichia coli*," *Proc. Natl. Acad. Sci. USA 85*:9674–9678 (1988).

Radicella, J. P. et al., "Patch Length of Localized Repair Events: Role of DNA Polymerase I in mutY–Dependent Mismatch Repair," *J. Bacteriol. 175*:7732–7736 (1993).

Radman, M. and Wagner, R., "Mismatch Repair in *Eschericia Coli*," *Ann. Rev. Genet. 20*:523–538 (1986).

Raposa, S. and Fox, M. S., "Some Features of Base Pair Mismatch and Heterology Repair in *Escherichia Coli*," *Genetics 117*:381–390 (1987).

Sakumi et al., "Cloning and Expression of cDNA for a Human Enzyme that Hydrolyzes 8–oxo–dGTP, a Mutagenic Substrate for DNA Synthesis" *J. Biol. Chem. 268*:23524–23530 (1993).

Su, S. –S. et al., "Mispair Specificity of Methyl–directed DNA Mismatch Correction in Vitro," *J. Biol. Chem. 263*(14):6829–6835 (1988).

Tsai–Wu, J. –J. et al., "Nucleotide Sequence of the *Escherichia coli*. micA Gene Required for A/G–Specific Mismatch Repair: Identity of MicA and MutY," *J. Bacteriol. 173*:1902–1910 (1991).

Tsai–Wu, J. –J. et al., "*Escherichia coli* MutY protein has both N–glycosylase and apurinic/apyrimidinic endonuclease activities on A–C and A–G mispairs," *Proc. Natl. Acad. Sci. USA 89*:8779–8783 (1992).

Tsai–Wu, J.–J. and Lu, A.–L., "*Escherichia coli* mutY–dependent mismatch repair involves DNA polymerase I and a short repair tract," *Mol. Gen. Genet. 244*(4):444–450 (1994).

Xu, J.F. et al., "Determining the Site and Nature of DNA Mutations With the Cloned MutY Mismatch Repair Enzyme," *Carcinogenesis 17*:321–326 (1996).

Young, R.A. et al., "Efficient Isolation of Genes by Using Antibody Probes," *Proc. Natl. Acad. Sci. U.S.A. 80*:1194–1198 (1983).

International Search Report for International Application No. PCT/US96/03239 (Mailing Date: Jul. 19, 1996).

GenBank Report, Accession No. T09329, submitted by M. Adams, et al. (Aug. 1993).

GenBank Report, Accession No. T33107, submitted by M. Adams, et al. (Sep. 1995).

GenBank Report, Accession No. W14150, submitted by M. Marra, et al. (Sep. 1996).

GenBank Report, Accession No. AA306293, submitted by M. Adams, et al. (Apr. 1997).

GenBank Report, Accession No. AA409965, submitted by M. Ko, et al. (May 1997).

GenBank Report, Accession No. AA461247, submitted by L. Hillier, et al. (Jun. 1997).

GenBank Report, Accession No. AA510123, submitted by M. Marra, et al. (Jul. 1997).

GenBank Report, Accession No. W14774, submitted by M. Marra, et al. (Sep. 1996).

GenBank Report, Accession No. AA325423, submitted by M. Adams, et al. (Apr. 1997).

GenBank Report, Accession No. R08531, submitted by L. Hillier, et al. (Apr. 1995).

GenBank Report, Accession No. AA848080, submitted by Cancer Genome Anatomy Project (Apr. 1998).

GenBank Report, Accession No. AA861673, submitted by Cancer Genome Anatomy Project (Mar. 1998).

GenBank Report, Accession No. N24004, submitted by L. Hillier, et al. (Dec. 1995).

GenBank Report, Accession No. AA815101, submitted by Cancer Genome Anatomy Project (Mar. 1998).

GenBank Report, Accession No. AA813309, submitted by Cancer Genome Anatomy Project (Feb. 1998).

GenBank Report, Accession No. AA767487, submitted by Cancer Genome Anatomy Project (Feb. 1998).

GenBank Report, Accession No. AA349792, submitted by M. Adams, et al. (Apr. 1997).

GenBank Report, Accession No. AA765650, submitted by Cancer Genome Anatomy Project. (Feb. 1998).

GenBank Report, Accession No. R49993, submitted by L. Hillier, et al. (May 1995).

GenBank Report, Accession No. AA409964, submitted by M. Ko, et al. (May 1997).

GenBank Report, Accession No. W57585, submitted by L. Hillier, et al. (Oct 1996).

GenBank Report, Accession No. AA847446, submitted by Cancer Genome Anatomy Project (Mar. 1998).

GenBank Report, Accession No. AA516416, submitted by Cancer Genome Anatomy Project (Aug. 1997).

GenBank Report, Accession No. AA534096, submitted by Cancer Genome Anatomy Project (Aug. 1997).

GenBank Report, Accession No. H07650, submitted by Sohn, U. et al. (Jun. 1995).

```
CTAGTT  CAGGC  GGAAG  GAGCA  GTCCT  CTGAA  GCTTG          -171
AGGAG  CCTCT  AGAAC  TATGA  GCCCG  AGGCC  TTCCC  CTCTC  CCAGA   -135
GCGCA  GAGGC  TTTGA  AGGCT  ACCTC  TGGGA  AGCCG  CTCAC  CGTCG    -90
GAAGC  TGCGG  GAGCT  GAAAC  TGCGC  CATCG  TCACT  GTCGG  CGGCC    -45

ATG  ACA  CCG  CTC  GTC  TCC  CGC  CTG  AGT  CGT  CTG  TGG  GCC  ATC    42
 M    T    P    L    V    S    R    L    S    R    L    W    A    I    14

ATG  AGG  AAG  CCA  CGA  GCA  GCC  GTG  GGA  AGT  GGT  CAC  AGG  AAG    84
 M    R    K    P    R    A    A    V    G    S    G    H    R    K    28

CAG  GCA  GCC  AGC  CAG  GAA  GGG  AGG  CAG  AAG  CAT  GCT  AAG  AAC   126
 Q    A    A    S    Q    E    G    R    Q    K    H    A    K    N    42

AAC  AGT  CAG  GCC  AAG  CCT  TCT  GCC  TGT  GAT  GGC  CTG  GCC  AGG   168
 N    S    Q    A    K    P    S    A    C    D    G    L    A    R    56

CAG  CCG  GAA  GAG  GTG  GTA  TTG  CAG  GCC  TCT  GTC  TCC  TCA  TAC   210
 Q    P    E    E    V    V    L    Q    A    S    V    S    S    Y    70

CAT  CTA  TTC  AGA  GAC  GTA  GCT  GAA  GTC  ACA  GCC  TTC  CGA  GGG   252
 H    L    F    R    D    V    A    E    V    T    A    F    R    G    84

AGC  CTG  CTA  AGC  TGG  TAC  GAC  CAA  GAG  AAA  CGG  GAC  CTA  CCA   294
 S    L    L    S    W    Y    D    Q    E    K    R    D    L    P    98

TGG  AGA  AGA  CGG  GCA  GAA  GAT  GAG  ATG  GAC  CTG  GAC  AGG  CGG   336
 W    R    R    R    A    E    D    E    M    D    L    D    R    R   112

GCA  TAT  GCT  GTG  TGG  GTC  TCA  GAG  GTC  ATG  CTG  CAG  CAG  ACC   378
 A    Y    A    V    W    V    S    E    V    M    L    Q    Q    T   126

CAG  GTT  GCC  ACT  GTG  ATC  AAC  TAC  TAT  ACC  GGA  TGG  ATG  CAG   420
 Q    V    A    T    V    I    N    Y    Y    T    G    W    M    Q   140

AAG  TGG  CCT  ACA  CTG  CAG  GAC  CTG  GCC  AGT  GCT  TCC  CTG  GAG   462
 K    W    P    T    L    Q    D    L    A    S    A    S    L    E   154

GAG  GTG  AAT  CAA  CTC  TGG  GCT  GGC  CTG  GGC  TAC  TAT  TCT  CGT   504
 E    V    N    Q    L    W    A    G    L    G    Y    Y    S    R   168
```

FIG. 1A

```
GGC CGG CGG CTG CAG GAG GGA GCT CGG AAG GTG GTA GAG GAG    546
 G   R   R   L   Q   E   G   A   R   K   V   V   E   E    182

CTA GGG GGC CAC ATG CCA CGT ACA GCA GAG ACC CTG CAG CAG    588
 L   G   G   H   M   P   R   T   A   E   T   L   Q   Q    196

CTC CTG CCT GGC GTG GGG CGC TAC ACA GCT GGG GCC ATT GCC    630
 L   L   P   G   V   G   R   Y   T   A   G   A   I   A    210

TCT ATC GCC TTT GGC CAG GCA ACC GGT GTG GTG GAT GGC AAC    672
 S   I   A   F   G   Q   A   T   G   V   V   D   G   N    224

GTA GCA CGG GTG CTG TGC CGT GTC CGA GCC ATT GGT GCT GAT    714
 V   A   R   V   L   C   R   V   R   A   I   G   A   D    238

CCC AGC AGC ACC CTT GTT TCC CAG CAG CTC TGG GGT CTA GCC    756
 P   S   S   T   L   V   S   Q   Q   L   W   G   L   A    252

CAG CAG CTG GTG GAC CCA GCC CGG CCA GGA GAT TTC AAC CAA    798
 Q   Q   L   V   D   P   A   R   P   G   D   F   N   Q    266

GCA GCC ATG GAG CTA GGG GCC ACA GTG TGT ACC CCA CAG CGC    840
 A   A   M   E   L   G   A   T   V   C   T   P   Q   R    280

CCA CTG TGC AGC CAG TGC CCT GTG GAG AGC CTG TGC CGG GCA    882
 P   L   C   S   Q   C   P   V   E   S   L   C   R   A    294

CGC CAG AGA GTG GAG CAG GAA CAG CTC TTA GCC TCA GGG AGC    924
 R   Q   R   V   E   Q   E   Q   L   L   A   S   G   S    308

CTG TCG GGC AGT CCT GAC GTG GAG GAG TGT GCT CCC AAC ACT    966
 L   S   G   S   P   D   V   E   E   C   A   P   N   T    322

GGA CAG TGC CAC CTG TGC CTG CCT CCC TCG GAG CCC TGG GAC   1008
 G   Q   C   H   L   C   L   P   P   S   E   P   W   D    336

CAG ACC CTG GGA GTG GTC AAC TTC CCC AGA AAG GCC AGC CGC   1050
 Q   T   L   G   V   V   N   F   P   R   K   A   S   R    350

AAG CCC CCC AGG GAG GAG AGC TCT GCC ACC TGT GTT CTG GAA   1092
 K   P   P   R   E   E   S   S   A   T   C   V   L   E    364
```

FIG.1B

```
CAG CCT GGG GCC CTT GGG GCC CAA ATT CTG CTG GTG CAG AGG    1134
 Q   P   G   A   L   G   A   Q   I   L   L   V   Q   R     378

CCC AAC TCA GGT CTG CTG GCA GGA CTG TGG GAG TTC CCG TCC    1176
 P   N   S   G   L   L   A   G   L   W   E   F   P   S     392

GTG ACC TGG GAG CCC TCA GAG CAG CTT CAG CGC AAG GCC CTG    1218
 V   T   W   E   P   S   E   Q   L   Q   R   K   A   L     406

CTG CAG GAA CTA CAG CGT TGG GCT GGG CCC CTC CCA GCC ACG    1260
 L   Q   E   L   Q   R   W   A   G   P   L   P   A   T     420

CAC CTC CGG CAC CTT GGG GAG GTT GTC CAC ACC TTC TCT CAC    1302
 H   L   R   H   L   G   E   V   V   H   T   F   S   H     434

ATC AAG CTG ACA TAT CAA GTA TAT GGG CTG GCC TTG GAA GGG    1344
 I   K   L   T   Y   Q   V   Y   G   L   A   L   E   G     448

CAG ACC CCA GTG ACC ACC GTA CCA CCA GGT GCT CGC TGG CTG    1386
 Q   T   P   V   T   T   V   P   P   G   A   R   W   L     462

ACG CAG GAG GAA TTT CAC ACC GCA GCT GTT TCC ACC GCC ATG    1428
 T   Q   E   E   F   H   T   A   A   V   S   T   A   M     476

AAA AAG GTT TTC CGT GTG TAT CAG GGC CAA CAG CCA GGG ACC    1470
 K   K   V   F   R   V   Y   Q   G   Q   Q   P   G   T     490

TGT ATG GGT TCC AAA AGG TCC CAG GTG TCC TCT CCG TGC AGT    1512
 C   M   G   S   K   R   S   Q   V   S   S   P   C   S     504

CGG AAA AAG CCC CGC ATG GGC CAG CAA GTC CTG GAT AAT TTC    1554
 R   K   K   P   R   M   G   Q   Q   V   L   D   N   F     518

TTT CGG TCT CAC ATC TCC ACT GAT GCA CAC AGC CTC AAC AGT    1596
 F   R   S   H   I   S   T   D   A   H   S   L   N   S     532

GCA GCC CAG TGA CACCTCT GAAAG CCCCC ATTCC CTGAG AATC        1639
 A   A   Q                                                  535

CTGTTGTT AGTAAA GTGCTT ATTTTT GTAGTT AAAAAA AAAA AAAAAA     1687
```

FIG.1C

```
Human   63 LQASVSSYHLFRDVAEVTAFRGSLLSWYDQ.EKRDLPWRRRAEDEMDLDR 111
           :|||            .|.: :|.|||. :::.|||        ::|:
E.coli   1 MQAS.............QFSAQVLDWYDKYGRKTLPW........QIDK  28

112 RAYAVWVSEVMLQQTQVATVINYYTGWMQKWPTLQDLASASLEEVNQLWA 161
           :| ||:|||||||||||||| |:. :|.::||: |||.|.|:|| :||.
        29 TPYKVWLSEVMLQQTQVATVIPYFERFMARFPTVTDLANAPLDEVLHLWT  78

162 GLGYYSRGRRLQEGARKVVEELGGHMPRTAETLQQLLPGVGRYTAGAIAS 211
           |||||.|:|.|:..|..|..  ||..:| | |.:..  ||||||  |||||  |
        79 GLGYYARARNLHKAAQQVATLHGGKFPETFEEVAA.LPGVGRSTAGAILS 127

212 IAFGQATGVVDGNVARVLCRVRAIGADPSSTLVSQQLWGLAQQLVDPARP 261
           :.:|.   .::||||  |||.|.  |:::  |:..  |...||:|.:|:..:. .
       128 LSLGKHFPILDGNVKRVLARCYAVSGWPGKKEVENKLWSLSEQVTPAVGV 177

262 GDFNQAAMELGATVCTPQRPLCSQCPVESLCRARQRVEQEQLLASGSLSG 311
           :  ||||  |:|||   :||. :|  || ||:::.  | |
       178 ERFNQAMMDLGAMICTRSKPKCSLCPLQNGCIA................ 210

312 SPDVEECAPNTGQCHLCLPPSEPWDQTLGVVNFPRKASRKPPREESSATC 361
                  |:|.:    :.| |:.. .|||.                |...:
       211 .......AANNS...WALYPGKKPKQTLP...............ERTGYF 235

362 VLEQPGALGAQILLVQRPNSGLLAGLWEFPSVTWEPSEQLQRKALLQELQ 411
           :| |.    :.::||.||| |||::|||: || .. |.|       ||| |.
       236 LLLQH...EDEVLLAQRPPSGLWGGLYCFPQFADEES.......LRQWLA 275

412 RWAGPLPATHLRHLGEVVHTFSHIKLTYQVYGLALEGQTPVTTVPPGARW 461
            .:  .::|.:|  :|...  ||||:.|..    .|:::.|. .. . ...| |
       276 QR..QIAADNLTQLTAFRHTFSHFHLDIVPMWLPVSSFTGCMD.EGNALW 322

462 LTQEEFHTAAVSTAMKKVFRVYQGQQPG 489
           ..  .: ..............::::  .....|.
       323 YNLAQPPSVGLAAPVERLLQQLRTGAPV 350
```

FIG. 2

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1858 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CTAGTTCAGG CGGAAGGAGC AGTCCTCTGA AGCTTGAGGA GCCTCTAGAA CTATGAGCCC      60

GAGGCCTTCC CCTCTCCCAG AGCGCAGAGG CTTTGAAGGC TACCTCTGGG AAGCCGCTCA     120

CCGTCGGAAG CTGCGGGAGC TGAAACTGCG CCATCGTCAC TGTCGGCGGC CATGACACCG     180

CTCGTCTCCC GCCTGAGTCG TCTGTGGGCC ATCATGAGGA AGCCACGAGC AGCCGTGGGA     240
```

-continued

```
AGTGGTCACA GGAAGCAGGC AGCCAGCCAG GAAGGGAGGC AGAAGCATGC TAAGAACAAC      300

AGTCAGGCCA AGCCTTCTGC CTGTGATGGC CTGGCCAGGC AGCCGGAAGA GGTGGTATTG      360

CAGGCCTCTG TCTCCTCATA CCATCTATTC AGAGACGTAG CTGAAGTCAC AGCCTTCCGA      420

GGGAGCCTGC TAAGCTGGTA CGACCAAGAG AAACGGGACC TACCATGGAG AAGACGGGCA      480

GAAGATGAGA TGGACCTGGA CAGGCGGGCA TATGCTGTGT GGGTCTCAGA GGTCATGCTG      540

CAGCAGACCC AGGTTGCCAC TGTGATCAAC TACTATACCG GATGGATGCA GAAGTGGCCT      600

ACACTGCAGG ACCTGGCCAG TGCTTCCCTG GAGGAGGTGA ATCAACTCTG GGCTGGCCTG      660

GGCTACTATT CTCGTGGCCG GCGGCTGCAG GAGGGAGCTC GGAAGGTGGT AGAGGAGCTA      720

GGGGGCCACA TGCCACGTAC AGCAGAGACC CTGCAGCAGC TCCTGCCTGG CGTGGGGCGC      780

TACACAGCTG GGCCATTGC CTCTATCGCC TTTGCCAGG CAACCGGTGT GGTGGATGGC        840

AACGTAGCAC GGGTGCTGTG CCGTGTCCGA GCCATTGGTG CTGATCCCAG CAGCACCCTT      900

GTTTCCCAGC AGCTCTGGGG TCTAGCCCAG CAGCTGGTGG ACCCAGCCCG GCCAGGAGAT      960

TTCAACCAAG CAGCCATGGA GCTAGGGGCC ACAGTGTGTA CCCCACAGCG CCCACTGTGC     1020

AGCCAGTGCC CTGTGGAGAG CCTGTGCCGG GCACGCCAGA GAGTGGAGCA GGAACAGCTC     1080

TTAGCCTCAG GGAGCCTGTC GGGCAGTCCT GACGTGGAGG AGTGTGCTCC CAACACTGGA     1140

CAGTGCCACC TGTGCCTGCC TCCCTCGGAG CCCTGGGACC AGACCCTGGG AGTGGTCAAC     1200

TTCCCCAGAA AGGCCAGCCG CAAGCCCCCC AGGGAGGAGA GCTCTGCCAC CTGTGTTCTG     1260

GAACAGCCTG GGGCCCTTGG GGCCCAAATT CTGCTGGTGC AGAGGCCCAA CTCAGGTCTG     1320

CTGGCAGGAC TGTGGGAGTT CCCGTCCGTG ACCTGGGAGC CCTCAGAGCA GCTTCAGCGC     1380

AAGGCCCTGC TGCAGGAACT ACAGCGTTGG GCTGGGCCCC TCCCAGCCAC GCACCTCCGG     1440

CACCTTGGGG AGGTTGTCCA CACCTTCTCT CACATCAAGC TGACATATCA AGTATATGGG     1500

CTGGCCTTGG AAGGGCAGAC CCCAGTGACC ACCGTACCAC CAGGTGCTCG CTGGCTGACG     1560

CAGGAGGAAT TCACACCGC AGCTGTTTCC ACCGCCATGA AAAAGGTTTT CCGTGTGTAT      1620

CAGGGCCAAC AGCCAGGGAC CTGTATGGGT TCCAAAAGGT CCCAGGTGTC CTCTCCGTGC     1680

AGTCGGAAAA AGCCCCGCAT GGGCCAGCAA GTCCTGGATA ATTTCTTTCG GTCTCACATC     1740

TCCACTGATG CACACAGCCT CAACAGTGCA GCCCAGTGAC ACCTCTGAAA GCCCCCATTC     1800

CCTGAGAATC CTGTTGTTAG TAAAGTGCTT ATTTTTGTAG TTAAAAAAAA AAAAAAAA      1858
```

(2) INFORMATION FOR SEQ ID NO:2:

(i) SEQUENCE CHARACTERISTICS:
  (A) LENGTH: 535 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:2:

```
Met Thr Pro Leu Val Ser Arg Leu Ser Arg Leu Trp Ala Ile Met Arg
  1               5                  10                  15

Lys Pro Arg Ala Ala Val Gly Ser Gly His Arg Lys Gln Ala Ala Ser
                 20                  25                  30

Gln Glu Gly Arg Gln Lys His Ala Lys Asn Asn Ser Gln Ala Lys Pro
             35                  40                  45

Ser Ala Cys Asp Gly Leu Ala Arg Gln Pro Glu Glu Val Val Leu Gln
         50                  55                  60
```

-continued

```
Ala Ser Val Ser Ser Tyr His Leu Phe Arg Asp Val Ala Glu Val Thr
 65                  70                  75                  80

Ala Phe Arg Gly Ser Leu Leu Ser Trp Tyr Asp Gln Glu Lys Arg Asp
                 85                  90                  95

Leu Pro Trp Arg Arg Arg Ala Glu Asp Glu Met Asp Leu Asp Arg Arg
                100                 105                 110

Ala Tyr Ala Val Trp Val Ser Glu Val Met Leu Gln Gln Thr Gln Val
            115                 120                 125

Ala Thr Val Ile Asn Tyr Tyr Thr Gly Trp Met Gln Lys Trp Pro Thr
            130                 135                 140

Leu Gln Asp Leu Ala Ser Ala Ser Leu Glu Glu Val Asn Gln Leu Trp
145                 150                 155                 160

Ala Gly Leu Gly Tyr Tyr Ser Arg Gly Arg Arg Leu Gln Glu Gly Ala
                165                 170                 175

Arg Lys Val Val Glu Glu Leu Gly Gly His Met Pro Arg Thr Ala Glu
                180                 185                 190

Thr Leu Gln Gln Leu Leu Pro Gly Val Gly Arg Tyr Thr Ala Gly Ala
            195                 200                 205

Ile Ala Ser Ile Ala Phe Gly Gln Ala Thr Gly Val Val Asp Gly Asn
            210                 215                 220

Val Ala Arg Val Leu Cys Arg Val Arg Ala Ile Gly Ala Asp Pro Ser
225                 230                 235                 240

Ser Thr Leu Val Ser Gln Gln Leu Trp Gly Leu Ala Gln Gln Leu Val
                245                 250                 255

Asp Pro Ala Arg Pro Gly Asp Phe Asn Gln Ala Ala Met Glu Leu Gly
                260                 265                 270

Ala Thr Val Cys Thr Pro Gln Arg Pro Leu Cys Ser Gln Cys Pro Val
            275                 280                 285

Glu Ser Leu Cys Arg Ala Arg Gln Arg Val Glu Gln Glu Gln Leu Leu
            290                 295                 300

Ala Ser Gly Ser Leu Ser Gly Ser Pro Asp Val Glu Glu Cys Ala Pro
305                 310                 315                 320

Asn Thr Gly Gln Cys His Leu Cys Leu Pro Pro Ser Glu Pro Trp Asp
                325                 330                 335

Gln Thr Leu Gly Val Val Asn Phe Pro Arg Lys Ala Ser Arg Lys Pro
                340                 345                 350

Pro Arg Glu Glu Ser Ser Ala Thr Cys Val Leu Glu Gln Pro Gly Ala
            355                 360                 365

Leu Gly Ala Gln Ile Leu Leu Val Gln Arg Pro Asn Ser Gly Leu Leu
            370                 375                 380

Ala Gly Leu Trp Glu Phe Pro Ser Val Thr Trp Glu Pro Ser Glu Gln
385                 390                 395                 400

Leu Gln Arg Lys Ala Leu Leu Gln Glu Leu Gln Arg Trp Ala Gly Pro
                405                 410                 415

Leu Pro Ala Thr His Leu Arg His Leu Gly Glu Val Val His Thr Phe
            420                 425                 430

Ser His Ile Lys Leu Thr Tyr Gln Val Tyr Gly Leu Ala Leu Glu Gly
            435                 440                 445

Gln Thr Pro Val Thr Thr Val Pro Pro Gly Ala Arg Trp Leu Thr Gln
450                 455                 460

Glu Glu Phe His Thr Ala Ala Val Ser Thr Ala Met Lys Lys Val Phe
465                 470                 475                 480

Arg Val Tyr Gln Gly Gln Gln Pro Gly Thr Cys Met Gly Ser Lys Arg
```

```
                485              490              495
Ser Gln Val Ser Ser Pro Cys Ser Arg Lys Lys Pro Arg Met Gly Gln
            500              505              510

Gln Val Leu Asp Asn Phe Phe Arg Ser His Ile Ser Thr Asp Ala His
            515              520              525

Ser Leu Asn Ser Ala Ala Gln
            530          535
```

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:3:

CGCGGATCCG CCATCATTGA CACCGCTCGT CTCC                                  34

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:4:

GCGTCTAGAT CACTGGGCTG CACTGTTG                                        28

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:5:

CGCGGATCCC GCAATCATGA CACCGCTCGT CTCC                                  34

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:6:

GCGTCTAGAT CACTGGGCTG CACTGTTG                                        28

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:7:

CGCGGATCCG CCATCATGAC ACCGCTCGTC TCC                                   33

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:8:

GCGCTCGAGC TGGGCTGCAC TGTTGAGG                                                28

(2) INFORMATION FOR SEQ ID NO:9:

(i) SEQUENCE CHARACTERISTICS:
        (A) LENGTH: 350 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Gln Ala Ser Gln Phe Ser Ala Gln Val Leu Asp Trp Tyr Asp Lys
  1               5                  10                  15

Tyr Gly Arg Lys Thr Leu Pro Trp Gln Ile Asp Lys Thr Pro Tyr Lys
             20                  25                  30

Val Trp Leu Ser Glu Val Met Leu Gln Gln Thr Gln Val Ala Thr Val
         35                  40                  45

Ile Pro Tyr Phe Glu Arg Phe Met Ala Arg Phe Pro Thr Val Thr Asp
 50                  55                  60

Leu Ala Asn Ala Pro Leu Asp Glu Val Leu His Leu Trp Thr Gly Leu
 65                  70                  75                  80

Gly Tyr Tyr Ala Arg Ala Arg Asn Leu His Lys Ala Ala Gln Gln Val
             85                  90                  95

Ala Thr Leu His Gly Gly Lys Phe Pro Glu Thr Phe Glu Glu Val Ala
            100                 105                 110

Ala Leu Pro Gly Val Gly Arg Ser Thr Ala Gly Ala Ile Leu Ser Leu
            115                 120                 125

Ser Leu Gly Lys His Phe Pro Ile Leu Asp Gly Asn Val Lys Arg Val
        130                 135                 140

Leu Ala Arg Cys Tyr Ala Val Ser Gly Trp Pro Gly Lys Lys Glu Val
145                 150                 155                 160

Glu Asn Lys Leu Trp Ser Leu Ser Glu Gln Val Thr Pro Ala Val Gly
                165                 170                 175

Val Glu Arg Phe Asn Gln Ala Met Met Asp Leu Gly Ala Met Ile Cys
            180                 185                 190

Thr Arg Ser Lys Pro Lys Cys Ser Leu Cys Pro Leu Gln Asn Gly Cys
        195                 200                 205

Ile Ala Ala Asn Asn Ser Trp Ala Leu Tyr Pro Gly Lys Lys Pro
210                 215                 220

Lys Gln Thr Leu Pro Glu Arg Thr Gly Tyr Phe Leu Leu Leu Gln His
225                 230                 235                 240

Glu Asp Glu Val Leu Leu Ala Gln Arg Pro Pro Ser Gly Leu Trp Gly
            245                 250                 255

Gly Leu Tyr Cys Phe Pro Gln Phe Ala Asp Glu Glu Ser Leu Arg Gln
            260                 265                 270

Trp Leu Ala Gln Arg Gln Ile Ala Ala Asp Asn Leu Thr Gln Leu Thr
        275                 280                 285

Ala Phe Arg His Thr Phe Ser His Phe His Leu Asp Ile Val Pro Met
        290                 295                 300
```

Trp Leu Pro Val Ser Ser Phe Thr Gly Cys Met Asp Glu Gly Asn Ala
305                 310                 315                 320

Leu Trp Tyr Asn Leu Ala Gln Pro Pro Ser Val Gly Leu Ala Ala Pro
            325                 330                 335

Val Glu Arg Leu Leu Gln Gln Leu Arg Thr Gly Ala Pro Val
            340                 345                 350

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:10:

TCCTCTGAAG CTTGAGGAGC CTCTAGAACT                      30

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:11:

TAGCTCCATG GCTGCTTGGT TGAAA                            25

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:12:

GCCATCATGA GGAAGCCACG AGCAG                            25

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:13:

TAGCTCCATG GCTGCTTGGT TGAAA                            25

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:14:

TTGACCCGAA ACTGCTGAAT AG                                22

(2) INFORMATION FOR SEQ ID NO:15:

(i) SEQUENCE CHARACTERISTICS:

```
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:15:

CAGTGGAGAT GTGAGACCGA AAGAA                                              25

(2) INFORMATION FOR SEQ ID NO:16:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:16:

CAGCCCGGCC AGGAGATTTC AACCA                                              25

(2) INFORMATION FOR SEQ ID NO:17:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:17:

CAGTGGAGAT GTGAGACCGA AAGAA                                              25

(2) INFORMATION FOR SEQ ID NO:18:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:18:

CCCTCACTAA AGGGAACAAA AGCTGG                                             26
```

HUMAN MUTY

This application is a divisional of U.S. application Ser. No. 08/813,574, filed Mar. 7, 1997 (pending), which claims priority benefit to U.S. application Ser. No. 60/013,132, filed Mar. 11, 1996, the disclosures of both of which are herein incorporated by reference.

BACKGROUND OF THE INVENTION

The GO system includes 7,8-dihydro-8-oxoguanine, the structure of the predominant tautomeric form of the GO lesion. Oxidative damage can lead to GO lesions in DNA. MutY removes the misincorporated adenine from the A/GO mispairs that result from error-prone replication past the GO lesion. Repair polymerases are much less error-prone during trans lesion synthesis and can lead to a C/GO pair. Oxidative damage can also lead to 8-oxo-dGTP. Inaccurate replication could result in the misincorporation of 8-oxo-dGTP opposite template A residues, leading to A/GO mispairs. MutY could be involved in the mutation process because it is active on the A/GO substrate and would remove the template A, leading to the AT® CG transversions that are characteristic of a MutT strain. The 8-oxo-dGTP could also be incorporated opposite template cytosines, resulting in a damaged C/GO pair that could be corrected by MutM.

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as a human homologue of the *E. coli* MutY gene, sometimes hereinafter referred to as "hMYH".

Mismatches arise in DNA through DNA replication errors, through DNA recombination, and following exposure of DNA to deaminating or oxidating environments. Cells have a host of strategies that counter the thread to their genetic integrity from mismatched and chemically damaged base pairs (Friedberg, E. C., DNA repair, W. H. Freeman, New York (1985)). With regard specifically to mismatch repair of replication errors, *Escherichia coli* and *Salmonella typhimurium* direct the repair to the unmethylated newly synthesized DNA strand by dam methylation at d(GATC) sequences, using the MutHLS systems (Clavery, J. P and Lacks, S. A., Microbiol., Rev. 50:133–165 (1986); Modrich, P. Annu. Rev. Genet. 25:229–253 (1991); Radman, M. and R. Wagner, Annu. Rev. Genet. 20:523–528 (1986)). The very short patch pathway of *E. coli* is specific for a correction of T/G mismatches (a mismatch indicated by a slash) and is responsible for the correction of deaminated 5-methylcytosine (Jones, M., et al., Genetics, 115:605–610 (1987); Lieb, M., Mod. Gen. Genet. 181:118–125 (1983); Lieb, M., and D. Read, Genetics 114:1041–1060 (1986); Raposa, S. and N. S. Fox, Genetics 117:381–390 (1987)).

The *E. coli* MutY pathway corrects A/G and A/C mismatches, as well as adenines paired with 7,8-dihydro-8-oxo-deoxyguanine (8-oxoG or GO) (Au, K. G., et al., Proc. Natl. Acad. Sci USA 85:9163–9166 (1988); Lu, A. L. and D. Y. Chang, Genetics, 118:593–600 (1988); Michaels, M. L., et al., Proc. Natl. Acad. Sci. USA, 89:7022–7025 (1992); Michaels, M. L., et al., Biochemistry, 31:10964–10968 (1992); Radicella, J. P., et al., Proc. Natl. Acad. Sci. USA, 85:9674–9678 (1988); Su, S. -S., et al., J. Biol. Chem 263:6829–6835 1988). The 39-kDa MutY protein shares some homology with *E. coli* endonuclease III and contains a $[4Fe-4S]^{2+}$ cluster (Lu, A. -L., et al., 1994, Unpublished data; Michaels, M. L., et al., Nucleic Acids Res. 18:3841–3845 (1990); Tsai-Wu, J. -J., et al., Proc, Natl. Acad. Sci. USA 89:8779–8783 (1992); Tsai-Wu, J. -J., et al., J. Bacteriol. 173:1902–1910 (1991)). The MutY preparation of Tsai-Wu et al. (Tsai-Wu, J. -J., et al., Proc. Natl. Acad. Sci. USA 89:8779–8783 (1992)) has both DNA N-glycosylase and apurinic or apyrimidinic (AP) endonuclease activities, whereas those purified by Au et al. (Au K. G., et al., Proc. Natl. Acad. Sci. USA, 86:8877–8881 (1989), and Michaels et al. (Michaels, M. L., et al., Proc. Natl. Acad. Sci. USA, 89:7022–7025 (1992); Michaels, M. L., et al., Biochemistry, 31:10964–10968 (1992) possess only the glycosylase activity. DNA glycosylase specifically excises the mispaired adenine from the mismatch and the AP endonuclease cleaves the first phosphodiester bond 3¢ to the resultant AP site (Au K. G., et al., Proc. Nat. Acad. Sci. USA, 86:8877–8881 (1989); Tsai-Wu, J. -J., et al., Proc, Natl. Acad. Sci. USA 89:8779–8783 (1992).

Repair by the MutY pathway involves a short repair tract and DNA polymerase I (Radicella, J. P., et al., J. Bacteriol., 175:7732–7736 (1993); Tsai-Wu, J. -J., and A. -L. Lu, Mol. Gen. Genet. 244:444–450 (1994)).

The mismatch repair strategy detailed above has been evolutionarily conserved. Genetic analysis suggests that *Saccharomyces cerevisiae* has a repair system analogous to the bacterial dam methylation-dependent pathway (Bishop, D. K., et al., Nature (London) 243:362–364 (1987); Reenan, R. A. and R. D. Kolodner, Genetics, 132:963–973 (1992); Reenan, R. A. and R. D. Kolodner, Genetics, 132:975–985 (1992); Williamson, M., et al., Genetics 110:609–646 (1985)). This pathway is functionally homologous to the *E. coli* very sort patch pathway for the correction of deaminated 5-methylcytosine.

Two mutator genes in *E. coli*, the mutY and the mutM genes (Cabrera et al., J. Bacteriol., 170:5405–5407 (1988); and Nghiem, Y., et al., PNAS, USA, 85:9163–9166 (1988)) have been described, which work together to prevent mutations from certain types of oxidative damage, dealing in particular with the oxidized guanine lesion, 8-oxodGuanine (Michaels et al., PNAS, USA, 89:7022–7025 91992). In Michaels, M. L., and Miller, J. H., J. Bacteriol., 174:6321–6325 (1992) is a summary of the concerted action of these two enzymes, both of which are glycosylases. The MutM protein removes 8-oxodG from the DNA, and the resulting AP site is repaired to restore the G:C base pair. Some lesions are not repaired before replication, which results in 50% insertion of an A across from the 8-oxodG, which can lead to a G:C to T:A transversion at the next round of replication. However, the MutY protein removes the A across from 8-oxodG and repair synthesis restore a C most of the time, allowing the MutM protein another opportunity to repair the lesion. In accordance with this, mutators lacking either the MutM or MutY protein have an increase specifically in the G:G to T:A transversion (Cabrera et al., Id., (1988); and Nghiem, Y., et al., Id. (1988)), and cells lacking both enzymes have an enormous increase in this base substitution (Michaels et al., Id. (1992). A third protein, the product of the mutT gene, prevents the incorporation of 8-oxodGTP by hydrolyzing the oxidized triphosphate back to the monophosphate (Maki, H., and Sekiguchi, M., Nature, 355:273–275 91992)), preventing A:T to C:G transversions.

Accordingly, there exists a need in the art for identification and characterization of genes and proteins which modulate the human cellulare mutation rat, for use as, among other things, markers in cancer and diseases associated with DNA repair. In particular, there is a need for isolating and characterized human mismatch repair genes and proteins, which are essential to proper development and health of tissues and organs, such as the colon, and which can, among other things, play a role in preventing, ameliorating, diagnosing or correcting dysfunctions or disease, particularly cancer, and most particularly colon cancer, such as, for example, HNPCC (non-polyposis colon cancer).

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide, for therapeutic purposes, for example, to repair oxidative damage to DNA and prevent mutations from oxidative lesions, treat genetic diseases related to a mutated hMYH gene, for example, xerederma pigmentosum and neoplasia, and to diagnose an abnormal transformation of cells, particularly cancer, and most particularly colon cancer, such as for example HNPCC, and/or to diagnose a susceptibility to abnormal transformation of cells, particularly cancer, and most particularly colon cancer, such as for example NHPCC.

In accordance with yet a further aspect of the present invention, there are provided antibodies against such polypeptides.

In accordance with yet a further aspect of the present invention, there is also provided nucleic acid probes comprising nucleic acid molecules of sufficient length to specifically hybridize to a nucleic acid sequence of the present invention.

In accordance with still another aspect of the present invention, there are provided diagnostic assays for detecting diseases or susceptibility to diseases related to mutations in the nucleic acid sequences encoding a polypeptide of the present invention. In accordance with a further aspect of the invention is a process for diagnosing a cancer comprising determining from a sample derived from a patient a decreased level of activity of polypeptide having the sequence of SEQ ID NO:2.

In accordance with a further aspect of the invention is a process for diagnosing a cancer comprising determining from a sample derived from a patient a decreased level of expression of a gene encoding a polypeptide having the sequence of SEQ ID NO:2.

In accordance with a further aspect of the invention is a process for diagnosing a cancer comprising determining from a sample derived from a patient a decreased level of activity of polypeptide having the sequence of SEQ ID NO:9.

In accordance with a further aspect of the invention is a process for diagnosing a cancer comprising determining from a sample derived from a patient a decreased level of expression of a gene encoding a polynucleotide having the sequence of SEQ ID NO:9.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE DRAWINGS

FIGS. 1A–1C an illustration of the cDNA (SEQ ID NO:1) and corresponding deduced amino acid (SEQ ID NO:1) sequence of the polypeptide of the present invention. The nucleotide sequence of hMYH is shown with the numbering relative to the A of the ATG translation start site (+1). The amino acid sequence is shown below in single letter code and is also numbered in the margin.

FIG. 2 is an amino acid sequence comparison between the polypeptide of the present invention (SEQ ID NO:2) (top line) and *E. coli* MutY protein (SEQ ID NO:9) (bottom line).

In accordance with an aspect of the present invention, there is provided an isolated nucleic acid (polynucleotide) which encodes for the mature polypeptide having the deduced amino acid sequence of FIG. 1 (SEQ ID NO:2).

The polynucleotide of this invention may be obtained from numerous tissues of the human body, including brain and testes. The polynucleotide of this invention was discovered in a cDNA library derived from a human cerebellum. The cDNA clone for hMYH was deposited on Dec. 20, 1995 at the American Type Culture Collection, Patent Depository, 10801 University Boulevard, Manassas, Va. 20110-2209, and given accession number 97389. The hMYH gene contains 15 introns, and is 7.1 kb long. The 16 exons encode a nuclear protein of 535 amino acids that displays 41% identity to the *E. coli* MutY protein, which provides an important function in the repair of oxidative damaged DNA, and helps to prevent mutations from oxidative lesions. The hMYH gene maps on the short arm of chromosome 1, between p32.1 and p34.3. There is extensive homology between the hMYH protein and the *E. coli* MutY protein with extensive homology near the beginning of the *E. coli* protein, which is characterized by a string of 14 identical amino acids.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or may be a different coding sequence which coding sequence, as a result of the redundancy or degeneracy of the genetic code, encodes the same mature polypeptide as the DNA of FIG. 1 (SEQ ID NO:1).

The polynucleotide which encodes for the mature polypeptide of FIG. 1 (SEQ ID NO:2) may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2). The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) as well as variants of such polynucleotides which variants encode for a fragment, derivative or analog of the polypeptide of FIG. 1 (SEQ ID NO:2). Such nucleotide variants include deletion variants, substitution variants and addition or insertion variants. Certain specific variants, among other, are provided by the present invention, such as, an isolated nucleic acid having a sytosine (C) at position 366 and/or position 729 of the nucleotide sequence of FIG. 1 (SEQ ID NO:1). Certain other specific variants, among other, are provided by the present invention, such as, an isolated nucleic acid having a cytosine (C) at position 1095 of the nucleotide sequence of FIG. 1 (SEQ ID NO:1). Further specific variants include, but are not limited to, an isolated polypeptide sequence having a glutamine (Q) at position 365 of the amino acid sequence in FIG. 1 (SEQ ID NO:2).

As hereinabove indicated, the polynucleotide may have a coding sequence which is a naturally occurring allelic variant of the coding sequence shown in FIG. 1 (SEQ ID NO:1). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE vector to provide for purification of the mature polypeptide fused to the marker in the case of a bacterial host, or, for example, the marker sequence may be a hemaglutinin (HA) tag when a mammalian host, e.g. COS-7 cells, is used. The HA tag corresponds to a epitope derived from the influenza hemaglutinin protein (Wilson, I., et al., Cell, 37:767 (1984)).

The term "gene" means the segment of DNA involved in producing a polypeptide chain; it included regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type have at least 15 bases, preferably 30 bases and most preferably 50 or more bases. The probe may also be used to identify a cDNA clone corresponding to a full length transcript and agenomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequence if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1).

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

This, the present invention is directed to polynucleotides having at least a 70% identity, preferably at least 90% and more preferably at least a 95% identity to a polynucleotide which encodes the polypeptide of SEQ ID NO:2 and polynucleotides complementary thereto as well as portions thereof, which portions have at least 15 consecutive bases, preferably 30 consecutive bases and most preferably at least 50 consecutive bases and to polypeptides encoded by such polynucleotides.

The present invention further relates to a polypeptide which has the deduced amino acid sequence of FIG. 1 (SEQ ID NO:2), as well as fragments, analogs and derivatives of such polypeptide.

The terms "fragment," "derivative" and "analog" when referring to the polypeptide of FIG. 1 (SEQ ID NO:2) means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identify) to the polypeptide of SEQ ID NO:2 and more preferably at least 90% similarity (more preferably at least 90% identify) to the polypeptide of SEQ ID NO:2 and still more preferably at least 95% similarity (still more preferably at least 95% identify) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotides sequences as determined by the identity of the match between two strings of such sequences. Both identity and similarity can be readily calculated. While there exist a number of methods to measure identity and similarity between two polynucleotide or polypeptide sequences, the terms "identity" and "similarity" are well known to skilled artisans (Carillo, H., and Lipman, D., SIAM J. Applied Math., 48: 1073 (1988). Methods commonly employed to determine identity or similarity between two sequences include, but are not limited to disclosed in Guide to Huge Computers, Martin J. Bishop, ed., Academic Press, San Diego, 1994, and Carillo, H., and Lipman, D., SIAM J. Applied Math., 48: 1073 (1988). Preferred methods to determine identity are designed to give the largest match between the two sequences tested. Methods to determine identity and similarity are codified in computer programs. Preferred computer program methods to determine identity and similarity between two sequences include, but are not limited to, BLASTP, BLASTN, FASTA.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudoabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli$, lac or trp, the phase lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.coli$.

The vector containing the appropriate DNA sequence as hereinabove described, as well as an appropriate promoter or control sequence, ay be employed to transform an appropriate host to permit the host to express the protein.

As representative examples of appropriate hosts, there may be mentioned: bacterial cells, such as $E.\ coli$, Streptomyces, *Salmonella typhimurium*; fungal cells, such as yeast; insect cells such as *Drosophila S2* and *Spodoptera Sf9*; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99A, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cells, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E.coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Basillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by an convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The fragments, analogs and derivatives of the polypeptides of the present invention may be assayed for determination of mismatch-nicking activity and glycosylase activity. As an example of such an assay, protein samples are incubated with 1.8 fmol of either a 5'-end-labeled 116-mer, a 3'-end-labeled 120-mer, or a 3'-end-labeled 20-mer duplex DNA containing mismatches (see Yeh, Y. -C., et al., 1991, J. Bio. Chem. 266:6480–6486); (Roelen, H. C. P. F., et al., 1991, Nucleic Acids Res. 19:4361–4369) in a 20 ml reaction mixture containing 10 mM Tris-HCl (pH 7.6), 5 nM $ZnCl_2$, 0.5 mM DTT, 0.5 nM EDTA, and 1.5% glycerol. Following a 2 hour incubation at 37° C., the reaction products are lyophilized and dissolved in a solution containing 3 ml of 90% (vol/vol) formamide, 10 mM EDTA, 0.1% (wt/vol) xylene cyanol, and 0.1% (wt/vol) bromophenol blue. After heating at 90° C. for 3 minutes, DNA samples are analyzed on 8% polyacrylamide-8.3M urea DNA sequencing gels (Maxam, A. M. and W. Gilbert, 1980, Methods Enzymol., 65:499–560), and the gel was then autoradiographed. The DNA glycosylase activity was monitored by adding piperidine, after the enzyme incubation, to a final concentration of 1M. After 30 minutes of incubation at 90° C., the reaction products are analyzed as described above.

An Enzyme binding assay may also be performed wherein protein-DNA complexes are analyzed on 4% polyacrylamide gels in 50 mM Tris-borate (pH 8.3) and 1 mM EDTA. Protein samples are incubated with 3'-end-labeled 20-bp oligonucleotides as in the nicking assay, except 20 ng or poly(dI-dC) is added to each reaction mixture. Bovine serine albumin (1 mg) is added as indicated to the binding assay. For the binding competition assay, in addition to the 1.8 fmol of labeled 20-mer substrates, unlabeled 19-mer DNAs containing A/G, A/GO, or C-G pairings are added in excess of up to 180 fmol.

The invention provides a process for diagnosing a disease, particularly cancer, comprising determining from a sample derived from a patient a decreased level of activity of polypeptide having the sequence of FIG. 1 (SEQ ID NO:2). Decreased activity may be readily measured by one skilled in the art, for example determining the presence of an amino acid variation from the sequence in FIG. 1 (SEQ ID NO:2) followed by using the aforementioned enzyme binding assay or by measurement mismatch-nicking activity and glycosylase activity. The invention also provides a process for diagnosing a cancer comprising determining from a sample derived from a patient a decreased level of expression of polypeptide having the sequence of FIG. 1 (SEQ ID NO:2). Decreased protein expression can be measured using, on known quantities of protein, the aforementioned enzyme binding assay or by measurement mismatch-nicking activity and glycosylase activity and comparing these activities to known quantities of non-variant hMYH polypeptide.

The hMYH polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcome Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and b-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter, the ApoAI promoter; human globin promoters; viral thymidine kinase promoters, such as the Herpes Simplex thymidine kinase promoter; retroviral LTRs (including the modified retroviral LTRs hereinabove described ); the b-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, y-2, y-AM, PA12, T19-14X, VT-19-17-H2, yCRE, yCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Once the hMYH gene is being expressed intracellularly, it may be employed to repair DNA mismatches and therefore, prevent cells for uncontrolled growth and neoplasia such as occurs in cancer and tumors.

The hMYH gene and gene product of the present invention may be employed to treat patients who have a defect in the hMYH gene. Among the disorders which may be treated in such cases in cancer, and most particularly colon cancer, such as for example HNPCC, as well as xerederma pigmentosum.

hMYH may also be employed to repair oxidative damage to and oxidation of DNA and prevent mutations from oxidative lesions and other modifications of DNA that can be repaired by hMYH. Skilled artisans will be able to use the DNA repair assays of the invention to determine which defects and/or modifications of DNA can be repaired by hMYH.

In accordance with a further aspect of the invention, there is provided a process for determining susceptibility to cancer, and particularly colon cancer, and most particularly HNPCC. Thus, a mutation in hMYH indicates a susceptibility to cancer, and the nucleic acid sequences described above may be employed in an assay for ascertaining such susceptibility. Thus, for example, the assay may be employed to determine a mutation in a human DNA repair protein as herein described, such as a deletion, truncation, insertion, frame shift, etc., with such mutation being indicative of a susceptibility to cancer.

A mutation may be ascertained for example, by a DNA sequencing assay. Tissue samples, including but not limited to blood samples are obtained from a human patient. The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the DNA repair protein of the invention. The primer sequence is generally comprised of at least 15 consecutive bases, and may contain at least 30 or even 50 consecutive bases.

Individual carrying mutations in the gene of the present invention may also be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RT-PCR can also be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding hMYH can be used to identify and analyze mutations. Examples of representative primers are shown below in Table 1. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

TABLE 1

Primers used for detection of mutations in hMYH gene

| | | SEQ ID NO: |
|---|---|---|
| 1 5' | TCCTCTGAAGCTTGAGGAGCCTCTAGAACT 3' | 10 |
| 2 5' | TAGCTCCATGGCTGCTTGGTTGAAA 3' | 11 |
| 3 5' | GCCATCATGAGGAAGCCACGAGCAG 3' | 12 |
| 4 5' | TAGCTCCATGGCTGCTTGGTTGAAA 3' | 13 |
| 5 5' | TTGACCCGAAACTGCTGAATAG 3' | 14 |
| 6 5' | CAGTGGAGATGTGAGACCGAAAGAA 3' | 15 |
| 7 5' | CAGCCCGGCCAGGAGATTTCAACCA 3' | 16 |
| 8 5' | CAGTGGAGATGTGAGACCGAAAGAA 3' | 17 |
| 9 5' | CCCTCACTAAAGGGAACAAAAGCTGG 3' | 18 |

The above primers may be used for amplifying hMYH cDNA isolated from a sample derived from a patient. The invention also provides the primers of Table 1 with 1, 2, 3 or 4 nucleotides removed from the 5' and/or the 3' end. The primers may be used to amplify the gene isolated from the patient such that the gene may then be subject to various techniques for elucidation of the DNA sequence. In this way, mutations in the DNA sequence may be diagnosed.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence and/or quantitation of the level of the sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA. The invention provides a process for diagnosing, disease, particularly a cancer, and most particularly colon cancer, such as for example HNPCC, comprising determining from a sample derived from a patient a decreased level of expression of polynucleotide having the sequence of FIG. 1 (SEQ ID NO: 1). Decreased expression of polynucleotide can be measured using any on of the methods well known in the art for the quantation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Fluorescence in situ hybridization (FISH) of a cDNA clone to a metaphase chromosomal spread can be used to provide a precise chromosomal location.

As an example of how this was performed, hMYH DNA was digested and purified with QIAEX II DNA purification kit (QLAGEN, Inc., Chatsworth, Calif.) and ligated to Super Cos1 cosmid vector (STRATAGENE, La Jolla, Calif.). DNA was purified using Qiagen Plasmid Purification Kit (QIAGEN Inc., Chatsworth, Calif.) and 1 mg was labeled by nick translation in the presence of Biotin-dATP using BioNick Labelling Kit (GibcoBRL, Life Technologies Inc., Gaithersburg, Md.). Biotinilation was detected with GENETECT Detection System (CLONTECH Laboratories, Inc. Palo Alto, Calif.) In situ Hybridization was performed on slides using ONCOR Light Hybridization Kit (ONCOR, Gaithersburg, Md.) to detect single copy sequences on metaphase chromosomes. Peripheral blood of normal donors was cultured for three days in RPMI 1640 supplemented with 20% FCS, 3% PHA and penicillin/streptomycin, synchronized with $10^{-7}$M methotrexate for 17 hours and washed twice with unsupplemented RPMI. Cells were incubated with $10^{-3}$M thymidine for 7 hours. The cells were arrested in metaphase after 20 minutes incubation with colcemid (0.5 mg/ml) followed by hypotonic lysis in 75 mM KCl for 15 minutes at 37° C. Cell pellets were then spun out and fixed in Carnoy's fixative (3:1 methanol/acetic acid).

Metaphase spreads were prepared by adding a drop of the suspension onto slides and aid dried. Hybridization was performed by adding 100 ng of probe suspended in 10 ml of hybridization mix (50% formamide, 2×SSC, 1% dextran sulfate) with blocking human placental DNA 1 mg/ml), Probe mixture was denatured for 10 minutes in 70° C. water bath and incubated for 1 hour at 37° C., before placing on a prewarmed (37° C.) slide, which was previously denatured in 70% formamide/2×SSC at 70° C., and dehydrated in ethanol series, chilled to 4° C.

Slides were incubated for 16 hours at 37° C. in a humidified chamber. Slides were washed in 50% formamide/2× SSC for 10 minutes at 41° C. and 2×SSC for 7 minutes at 37° C. Hybridization probe was detected by incubation of the slides with FITC-Avidin (ONCOR, Gaithersberg, Md.), according to the manufacturer protocol. Chromosomes were counterstained with proporidium iodine suspended in mounting medium. Slides were visualized using a Leitz ORTHOPLAN 2-epifluorescence microscope and five computer images were taken using Imagenetics Computer and MacIntosh printer. hMYH maps to the short arm of chromosome 1, between p32.1 and p34.3.

Once a sequence has been mapped to a precise chromosomal location, the physical position of the sequence on the chromosome can be correlated with genetic map data. Such data are found, for example, in V. McKusick, Mendelian Inheritance in Man (publicly available on line via computer). The relationship between genes and diseases that have ben mapped to the same chromosomal region are then identified through linkage analysis (Co-Inheritance of Physically Adjacent Genes).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 ml of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 mg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of hMYH

The DNA sequence encoding hMYH is initially amplified using PCR oligonucleotide primers corresponding to the 5' sequences of the processed hMYH protein (minus the signal peptide sequence) and the vector sequences 3' and the mMYH gene. Additional nucleotides corresponding to hMYH were added to the 5' and 3' sequences respectively. The 5' oligonucleotide primer has the sequence 5' CGCG-GATCCGCCATCATGACACCGCTCGTCTCC 3' (SEQ ID NO:3) contains a BamHI restriction enzyme site followed by 18 nucleotides of hMYH coding sequence starting from the presumed terminal amino acid of the processed protein condon. The 3' sequence 5' GCGTCTAGATCACTGGGCT-GCACTGTTG 3' (SEQ ID NO:4) contains complementary sequences to XbaI site and is followed by 19 nucleotides of hMYH. The restriction enzyme sites correspond to the restriction enzyme sites on the bacterial expression vector pQE-9 (Qiagen, Inc. 9259 Eton Avenue, Chatsworth, Calif., 91311)). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 then is digested with BamHI and XbaI. The amplified sequences are ligated into pQE-9 and were inserted in frame with the sequence encoding for the histidine tag and the RBS. The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$_{.0.600}$) of between 0.4 and 0.6. IPTG ("Isopropyl-B-D-thiogalacto pyranoside") is then added to a final concentration of 1 nM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized hMYH is purified from this solution by chromatography on a Nickel-Chelate column under conditions that allow for tight binding by proteins containing the 6-His (histidine) tag (Hochuli, E. et al., J. Chromatography 411:177–184 (1984)). hMYH is eluted from the column in 6 molar guanidine HCl pH 5.0 and for the purpose of renaturation adjusted to 3 molar guanidine HCl, 100 nM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Cloning and Expression of hMYH Using the Baculovirus Expression System

The DNA sequence encoding the full length hMYH protein was amplified using PCR oligonucleotide primers corresponding to the 5' and 3' sequences of the gene:

The 5' primer has the sequence 5' CGCGGATCCCGA-CAATCATGACACCGCTCGTCTCC 3' (SEQ ID NO:5) and contains a BamHI restriction enzyme site (in bold) followed by 18 nucleotides resembling an efficient signal for the initiation of translation in eukaryotic cells (Kozak, J., J. Mol. Biol., 196:947–950 (1987) which is just behind the first 6 nucleotides of the hMYH gene (the initiation codon for translation "ATG" is underlined).

The 3' primer has the sequence 5' GCGTCTAGAT-CACTGGGCTGCACTGTTG 3' (SEQ ID NO:6) and contains the cleavage site for the restriction endonuclease XbaI and a number of nucleotides complementary to the 3' non-translated sequence of the hMYH gene sufficient for stable hybridization. The amplified sequences were isolated from a 1% agarose gel using a commercially available kit ("Geneclean," BIO 101 Inc., La Jolla, Calif.). The fragment was then digested with the endonucleases BamHI and XbaI and then purified again on a 1% agarose gel. This fragment is designated F2.

The vector pA2 (modification of pVL941 vector, discussed below) is used for the expression of the hMYH protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and XbaI. The polyadenylation site of the simian virus SV40 is used for efficient polyadenylation. For any easy selection of recombinant virus the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2 such as pAc373, pVL941, pRG1 and pAcIM1 (Luckow, V. A. and Summers, M. D., Virology, 170:31–39).

The plasmid is digested with the restriction enzymes BamHI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E.coli HB101 cells is then transformed and bacteris identified that contained the plasmid (pBachMYH) with the hMYH gene using the enzymes BamHI and XbaI. The sequence of the cloned fragment is confirmed by DNA sequencing.

5 mg of the plasmid pBachMYH is co-transfected with 1.0 mg of a commercially available linearized baculovirus ("BaculoGoldÔ baculovirus DNA", Pharmingen, San Diego, Calif.) using the lipofection method (Felgner et al. Proc. Natl. Acad. Sci. USA, 84:7413–7417 (1987)).

1 mg of BaculoGoldÔ virus DNA and 5 mg of the plasmid pBachMYH are mixed in a sterile well of a microtiter plate containing 50 ml of serum free Grace's medium (Life Technologies Inc., Gaithersburg, Md.). Afterwards 10 ml Lipofectin plus 90 ml Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used with allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus is added to the cells and blue stained plaques are picked with the tip of an Eppendorf pipette. The agar containing the recombinant viruses is then resuspended in an Eppendorf tube containing 200 ml of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-hMYH at a multiplicity of infection (MOI) of 2. Six hours later the medium is removed and replaced with SF900 II medium minus methionine and cysteine (Life Technologies Inc., Gaithersburg) 42 hours later 5 mCi of $^{35}$S-methionine and 5 mCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant hMYH in COS cells

The expression of plasmid, hMYH HA is derived from a vector pcDNAI/Amp (Invitrogen) containing: 1) SV40 origin of replication, 2) ampicillin resistance gene, 3) E.coli replication origin, 4) CMV promoter followed by a polylinker region, an SV40 intron and polyadenylation site. A DNA fragment encoding the entire hMYH precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding hMYH is constructed by PCR using two primers: the 5' primer 5'-CGCGGATCCGCCATCATGACACCGCTCGTCTCC-3' (SEQ ID NO:7) contains a BamHI site followed by 18 nucleotides of hMYH coding sequence starting from the initiation codon; the 3' sequence 5'-GCGCTCGAGCTGGGCTGCACTGTTGAGC (SEQ ID NO:8) contains complementary sequences to XhoI site, translation stop codon, HA tag and the last 19 nucleotides of the hMYH coding sequence (not including the stop codon). Therefore, the PCR product contains a BamHI site, hMYH coding sequence and an XhoI site. The PCR amplified DNA fragment and the vector, pcDNAI/Amp (comprising an HA tag at the 3' end), are digested with BamHI and XhoI restriction enzyme and ligated. The ligation mixture is transformed into E. coli strain SURE (available from Stratagene Cloning Systems, La Jolla) the transformed culture is plated on ampicillin media plates and resistant colonies are selected. Plasmid DNA is isolated from transformants and examined by restriction analysis for the presence of the correct fragment. For expression of the recombinant hMYH, COS cells are transfected with the expression vector by DEAE-DEXTRAN method (J. Sambrook, E. Fritsch, T.

Maniatis, Molecular Cloning: A Laboratory Manual, Cold Spring Laboratory Press, (1989)). The expression of the hMYH HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 0.1% SDS, 1% NP-40, 0.5% DOC, 50 nM Tris, pH 7.5) (Wilson, I. recombinant protein with an antibody that recognizes the HA epitope.

The plasmid construction strategy is described as follows:

The DNA sequence encoding hMYH is constructed by PCR using two primers: the 5' primer 5'-CGCGGATCCGCCATCATGACACCGCTCGTCTCC-3' (SEQ ID NO:7) contains a BamHI site followed by 18 nucleotides of hMYH coding sequence starting from the initiation codon; the 3' sequence 5'-GCGCTCGAGCTGGGCTGCACieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polypeptide comprising amino acid residues selected from the group consisting of:
   (a) amino acid residues 1 to 535 of SEQ ID NO:2; and
   (b) amino acid residues 2 to 535 of SEQ ID NO:1.

2. The isolated polypeptide of claim 1, wherein said amino acid residues are (a).

3. The isolated polypeptide of claim 1, wherein said amino acid residues are (b).

4. The isolated polypeptide of claim 1, which is produced or contained in a recombinant cell.

5. The isolated polypeptide of claim 1, further comprising a heterologous polypeptide.

6. An isolated polypeptide comprising amino acid residues encoded by a polynucleotide which hybridizes at 37° C. in 50% formamide, 2×SSC, and 1% dextran sulfate followed by washing with 50% formamide, 2XSCC for 10 minutes at 41° C. and 2×SSC for 7 minutes at 37° C. To a reference polynucleotide having the nucleotide sequence of the coding region of SEQ ID NO:1 or the complement thereof, wherein said isolated polypeptide has the same activity as a polypeptide having the amino acid sequence of amino acids 1 to 535 of SEQ ID NO:2.

7. The isolated polypeptide of claim 6, which is produced or contained in a recombinant cell.

8. The isolated polypeptide of claim 6, further comprising heterologous polypeptide.

9. An isolated polypeptide comprising 30 contiguous amino acid residues of SEQ ID NO:2.

10. The isolated polypeptide of claim 9, comprising 50 contiguous amino acid residues of SEQ ID NO:2.

11. The isolated polypeptide of claim 9, which is produced or contained in a recombinant cell.

12. The isolated polypeptide of claim 9, further comprising a heterologous polypeptide.

13. A method for repairing DNA mismatches, comprising administering to a cell the polypeptide of claim 1.

14. A method for repairing DNA mismatches, comprising administering to a cell the polypeptide of claim 6.

* * * * *

UNITED STATES PATENT AND TRADEMARK OFFICE
CERTIFICATE OF CORRECTION

PATENT NO. : 6,051,222
DATED : April 18, 2000
INVENTOR(S) : Wei, Ying-Fei

Page 1 of 1

It is certified that error appears in the above-identified patent and that said Letters Patent is hereby corrected as shown below:

Column 4,
Line 18, please delete "an illustration of" and insert therein --illustrate--.
Line 19, after "amino acid" please delete "(SEQ ID NO:1)" and insert therein --(SEQ ID NO:2)--.

Column 33, Claim 1(b),
Line 50, please delete "SEQ ID NO:1" and insert therein --SEQ ID NO:2--.

Column 33, Claim 6,
Line 63, please delete "To" and insert therein --to--.

Signed and Sealed this

Third Day of July, 2001

Attest:

Attesting Officer

NICHOLAS P. GODICI
*Acting Director of the United States Patent and Trademark Office*

UNITED STATES PATENT AND TRADEMARK OFFICE
CERTIFICATE OF CORRECTION

PATENT NO.   : 6,051,222
DATED        : April 18, 2000
INVENTOR(S)  : Wei, Ying-Fei Page 1 of 1

It is certified that error appears in the above-identified patent and that said Letters Patent is hereby corrected as shown below:

<u>Title page,</u>
Item [57] ABSTRACT,
Line 6, please delete "mutation" and insert therein -- mutations --.

<u>Column 1,</u>
Line 22, please delete "Go" and insert therein -- GO --.

<u>Column 33, claim 6,</u>
Line 60, please delete "37°C." and insert therein -- 37°C --.
Line 62, please delete "2XSCC" and insert therein -- 2XSSC --.
Line 63, please delete "41°C." and insert therein -- 41°C. --; and please delete "37 °C." and insert therein -- 37 °C --.

Signed and Sealed this

Twenty-sixth Day of March, 2002

*Attest:*

*Attesting Officer*

JAMES E. ROGAN
*Director of the United States Patent and Trademark Office*